United States Patent
Kanayama

(10) Patent No.: US 7,122,212 B2
(45) Date of Patent: Oct. 17, 2006

(54) PROCESS FOR PRODUCING OILY COSMETICS

(75) Inventor: Masanori Kanayama, Chiba (JP)

(73) Assignee: Pure Green Co., Ltd., Tokyo (JP)

( * ) Notice: Subject to any disclaimer, the term of this patent is extended or adjusted under 35 U.S.C. 154(b) by 0 days.

(21) Appl. No.: 10/311,149

(22) PCT Filed: Jun. 13, 2001

(86) PCT No.: PCT/JP01/05020

§ 371 (c)(1),
(2), (4) Date: Dec. 13, 2002

(87) PCT Pub. No.: WO01/95865

PCT Pub. Date: Dec. 20, 2001

(65) Prior Publication Data

US 2003/0152601 A1  Aug. 14, 2003

(30) Foreign Application Priority Data

Jun. 14, 2000 (JP) .............................. 2000/178783
Mar. 9, 2001 (JP) .............................. 2001/66751

(51) Int. Cl.
*A61K 36/82* (2006.01)
*A61K 8/02* (2006.01)
*A61K 8/92* (2006.01)
*A61K 8/97* (2006.01)

(52) U.S. Cl. ...................... 424/729; 424/400; 424/401; 424/725; 424/774

(58) Field of Classification Search ................ 424/400, 424/401, 725, 729, 774; 426/542, 597, 425, 426/429, 435
See application file for complete search history.

(56) References Cited

U.S. PATENT DOCUMENTS

| | | | | | |
|---|---|---|---|---|---|
| 5,043,100 A | * | 8/1991 | Chang et al. | ................ | 252/398 |
| 5,527,552 A | * | 6/1996 | Todd, Jr. | ..................... | 426/541 |
| 5,687,922 A | * | 11/1997 | Takaoka | ..................... | 241/259 |

FOREIGN PATENT DOCUMENTS

| | | | |
|---|---|---|---|
| GB | 335901 A | | 10/1930 |
| GB | 1184922 | * | 3/1970 |
| JP | 2-69142 A | | 3/1990 |
| JP | 5-78231 A | | 3/1993 |
| JP | 6-254378 A | | 9/1994 |
| JP | 6-279758 A | | 10/1994 |
| JP | 7-196466 A | | 8/1995 |
| JP | 7-196534 A | | 8/1995 |
| JP | 8-81325 A | | 3/1996 |
| JP | 8-275728 A | | 10/1996 |
| JP | 9-255519 A | | 9/1997 |
| JP | 10-218784 A | | 8/1998 |
| JP | 11-49655 A | | 2/1999 |
| JP | 2000-63262 A | | 2/2000 |
| JP | 2000-128801 A | | 5/2000 |
| JP | 2001-107 A | | 1/2001 |
| JP | 2001-192695 A | | 7/2001 |
| JP | 2001-218558 A | | 8/2001 |
| JP | 2001-231493 A | | 8/2001 |

* cited by examiner

*Primary Examiner*—Johann Richter
*Assistant Examiner*—Marina Lamm
(74) *Attorney, Agent, or Firm*—Birch, Stewart, Kolasch & Birch, LLP

(57) ABSTRACT

It is intended to provide oily cosmetics (for example, oily cosmetics to be applied to the skin such as oily liniments, oily hair care products such as hair oils) which have excellent effects including an antibacterial effect and are yet safely usable by consumers sensitive to chemicals. Namely, oily cosmetics comprising oily bases such as vegetable oils, mineral oils or mixtures thereof together with tea leaf components.

5 Claims, No Drawings

PROCESS FOR PRODUCING OILY COSMETICS

This application is the national phase under 35 U.S.C. § 371 of PCT International Application No. PCT/JP01/05020 which has an International filing date of Jun. 13, 2001, which designated the United States of America.

TECHNICAL FIELD

This invention relates to oily cosmetics. More specifically, it relates to oily cosmetics to be applied to the skin such as oily liniments or oily hair care products such as hair oils.

BACKGROUND OF THE INVENTION

There have been known oily cosmetics comprising vegetable oils, mineral type oils or mixtures thereof. For example, oily cosmetics containing olive oil, mineral oils or camellia oil have been widely employed for preventing the skin or hair from drying and for moistening the same. In particular, olive oil has been frequently used in Western countries for maintaining the smoothness of the skin or preventing the skin from drying. Immediately after applying olive oil to the skin, however, the skin surface becomes oily and, therefore, miscellaneous bacteria in the air would stick thereon more frequently than the ordinary state. Thus, it is feared that such skin surface might serve as an adequate medium for the growth of the miscellaneous bacteria.

To solve this problem, it has been a practice to add antibacterial compounds to oily cosmetics. However, a large number of artificially synthesized chemicals sometimes cause eczema and skin fit in consumers highly sensitive to chemicals, which makes it necessary to use these oily cosmetics with care. Actually, most of these products are marketed in association with strict instructions.

It is an object of the present invention to provide oily cosmetics which are free from the above problem and thus can be safely used even by consumers highly sensitive to chemicals. This object can be achieved by providing oily cosmetics containing tea leaf components which are natural materials and a process for producing the same. The term "oily cosmetics" as used herein means cosmetics to be applied to the skin such as oily liniments or oily hair care products such as hair oils.

In addition to β-carotene, tocopherol (vitamin E), ascorbic acid, niacin, etc., tea leaves contain substances having purine base such as caffeine and essential oil components such as geraniol. Moreover, it is already known that tea leaves contain various tannins in a large amount. Among all, it is known that much catechins falling within the category called fused tannins are contained therein. As the results of recent studies on effects of catechins contained in tea leaves, it is reported that catechins have a bactericidal and antibacterial effect, a deodorizing effect, an effect of preventing atopic dermatitis, a hypotensive effect and the like.

Since catechins are soluble in water, a special treatment is required to dissolve a sufficient amount of catechins in an oily base (Japanese Patent Publication of unexamined Application No.279758/1994). There have been known cosmetics containing tea extract, for example, cosmetic oils obtained by blending tea extract and vitamin E to linoleic acid (Japanese Patent Publication of unexamined Application No. 78231/1993), cosmetics obtained by blending tea extract, disodium ethylenediaminetetraacetate, etc. with lipids containing highly unsaturated fatty acids such as linolenic acid (Japanese Patent Publication of unexamined Application No. 81325/1996), and antibacterial cosmetic compositions comprising as the essential components tea extract containing catechins, tea tree and thyme extract (Japanese Patent Publication of unexamined Application No. 63262/2000). However, there has been known no cosmetic comprising tea extract alone without any other active components.

The present invention aims at producing and providing oily cosmetics which have excellent properties including antibacterial activity and are mild to the skin by totally using various active components typified by catechins contained in tea leaves without resort to any chemicals such as emulsifiers.

DISCLOSURE OF THE INVENTION

The present invention relates to: (1) an oily cosmetic containing an oily base and tea leaf components which is obtained by dissolving the components extracted from tea leaves in the oily base, or adding ground tea leaves to the oily base and thus allowing the tea leaf components to migrate into the oily base; (2) the oily cosmetic as described in (1) which can be obtained by adding preliminarily ground tea leaves to the oily base and then finely powdering together with the oily base; (3) the oily cosmetic as described in (2) characterized in that the powdering treatment is carried out until the diameter of the tea leaf grains attains 1 to 40 μm; (4) the oily cosmetic as described in (2) characterized in that the powdering treatment is carried out until the diameter of the tea leaf grains attains 4 to 10 μm; (5) an oily cosmetic as described in any of (1) to (4) characterized in that the oily base comprises a vegetable oil, a mineral type oil or a mixture thereof; (6) the oily cosmetic as described in (5) characterized in that the vegetable oil is olive oil, coconut oil, camellia oil, peanut oil, palm oil or rapeseed oil; and (7) the oily cosmetic as described in (5) characterized in that the mineral type oil is a mineral oil.

The oily base usable in the oily cosmetics according to the present invention can be selected from among vegetable oils, mineral type oils and mixtures thereof. Examples of the vegetable oils include olive oil, camellia oil, peanut oil, rapeseed oil, coconut oil, palm oil and the like. Examples of the mineral type oils include mineral oils. Among all, olive oil, mineral oils, coconut oil, etc. maybe cited as preferable examples of the oily base of the oily cosmetics according to the present invention, since they have been commonly employed in the art.

The tea leaves to be used in the present invention are leaves of a plant *Thea sinensis* or its cultivation varieties. Processed tea leaves involve non-fermented tea such as green tea, fermented tea such as black tea, semifermented tea and incompletely fermented tea. Any of these tea leaves are usable as a material for producing the oily cosmetics according to the present invention. Since much catechins still remain in used tea leaves, it is also possible to employ used tea leaves as a starting material. That is to say, the term "tea leaves" as employed herein involves used tea leaves too.

Various embodiments can be considered as the process for producing the oily cosmetics according to the present invention. For example, a process for producing an oily cosmetic which comprises mixing components extracted from tea leaves with an oily base may be cited. It is also possible to cite a process which comprises finely powdering tea leaves and then immersing the same in an oily base to elute the tea leaf components therefrom.

The tea leaf components can be extracted by a conventional method. Namely, tea leaves are dried, powdered or cut into small pieces and then subjected a treatment with hot water, steam distillation or immersion in an alcohol or a mixture of an alcohol with water. Alternatively, tea leaves may be extracted with water at ordinary temperature for 1 to 10 days and then treated with an alcohol. In this case, catechol-rich components can be obtained in the form of a solution. The extract thus obtained is filtered, if needed, and the filtrate is concentrated optionally followed by drying. The concentration is generally carried out by distilling under reduced pressure. The drying may be carried out by an appropriate procedure selected from among spray drying, vacuum drying, freeze drying and so on.

The obtained tea leaf components are mixed with an oily base and dissolved therein. Thus, the oily cosmetic according to the present invention can be obtained. The mixing ratio may be appropriately varied. In usual, from 10 to 100 g, preferably from 20 to 50 g, of the tea leaf components are used per liter of the oily base. To dissolve the tea leaf components in the oily base, use may be made of physical means such as ultrasonication or high-speed agitation. The oily base containing the tea leaf components thus obtained may further contain, if needed, perfumes, etc.

In another example of the process for producing the oily cosmetic according to the present invention, tea leaves are directly added to the oily base so that the tea leaf components are allowed to migrate into the oily base. In this case, dried tea leaves are finely powdered and then mixed with the oily base so as to allow the tea leaf components to migrate into the oily base. Although the amount of the tea leaves varies depending on the type and conditions (for example, the extent of dryness), use may be made of from 30 to 800 g, preferably from 100 to 500 g and still preferably from 250 to 400 g of the tea leaves per liter of the oily base at ordinary temperature. The extraction time ranges from 3 to 48 hours, preferably from 6 to 24 hours and still preferably from 10 to 18 hours. After the completion of the extraction, the residue is filtered off and, if needed, other components such as perfumes are added. Thus, a liquid oily cosmetic (a liniment) can be obtained.

In the above-described production process, the preliminarily ground tea leaves may added to the oily base and then finely powdered. Thus, the migration of the tea leaf components into the oily base can be accelerated and, therefore, an oily cosmetic having the tea leaf components at a high concentration can be obtained. In this case, it is preferable to carry out the powdering until the diameter of the tea leaf grains attains 1 to 40 µm, preferably 4 to 10 µm. The powdering is performed for 5 to 20 minutes, preferably 10 to 15 minutes. After the completion of the powdering, the insoluble matters are eliminated by filtration or centrifugation to thereby give an oily cosmetic having the tea leaf components at a high concentration. The extraction effect can be particularly enhanced by separating with the use of a continuous centrifuge at from 6,000 to 13,500 rpm at a liquid supply rate of from 50 to 60 l/h. According to this process, the step of extracting the tea leaf components can be omitted and catechins and the like can be dissolved in the oily base at a high concentration. The oily solution thus obtained may further contain perfumes and so on, if needed.

BEST MODE FOR CARRYING OUT THE INVENTION

Now, the present invention will be described in greater detail by referring the following examples. However, it is to be understood that the present invention is not construed as being restricted thereto.

EXAMPLE 1

Process for Producing Liniment by Direct Extraction:

140 g of green tea leaves, which had been dried to give a moisture content of 5% or less, were powdered into 4- to 10 µm in friction grinder. Under stirring, the powdered tea leaves were added to 500 ml of olive oil maintained at 15 to 20° C. and extracted for 12 hours. During this period, the whole mixture was stirred at intervals of 1 to 2 hours. After the completion of the extraction, the residue was filtered off to give slightly greenish olive oil. Then this olive oil was poured in portions into containers to give an oily liniment. By replacing the olive oil employed as the oily base in the production process in this EXAMPLE by camellia oil or mineral oil, a hair care product or a baby oil can be respectively obtained.

When the slightly greenish olive oil obtained above was analyzed by high performance liquid chromatography, it was found out that the content of catechins therein was less than the lower detection limit but the contents of β-carotene, total ascorbic acid and total tocopherol were respectively 2.1 mg/100 g, 4 mg/100 g and 7.0 mg/100 g.

EXAMPLE 2

Process for Producing Liniment by Adding Components Extracted from tea leaves:

1 kg of green tea leaves, which had been dried to give a moisture content of 5% or less, were powdered into 4- to 18 µm in a friction grinder and then packed in a heat-circulatory extracting apparatus. Then the powdered tea leaves were extracted under circulation of 20 l of hot water (95 to 100° C.) for 1 hour. After cooling to room temperature, the extract was filtered to give 16 l of a filtrate. The filtrate was distilled under reduced pressure of about 100 mmHg at 50° C. or below for 6 hours to thereby give 0.8 l of a yellowish brown, somewhat viscous liquid. Next, it was spray-dried at an intake gas temperature of 160° and an exhaust gas temperature of 80° C. 130 g of the brown powder thus obtained was further powdered at a low temperature. 100 g of this fine powder contained from 30 to 50 g of catechins, from 2 to 4 g of caffeine, from 150 to 250 mg of vitamin C, from 13 to 29 mg of β-carotene and other trace components. The contents varied depending on the time of harvesting the tea leaves.

The whole extract (130 g) obtained above was added to 4 l of olive oil and dissolved therein by ultrasonically stirring (0.5 to 1.5 min) at 40 to 50° C. After filtering off the insoluble residue if any, slightly greenish olive oil was obtained. Then this olive oil was poured in portions into containers to give an oily liniment. By replacing the olive oil employed as the oily base in the production process in this EXAMPLE by camellia oil or mineral oil, a hair care product or a baby oil can be respectively obtained.

The slightly greenish olive oil obtained above was analyzed by high performance liquid chromatography. The results are as follows:

| | |
|---|---|
| epicatechin | 18 mg/100 g |
| epigallocatechin | 68 mg/100 g |
| epicatechin gallate | 18 mg/100 g |
| epigallocatechin gallate | 71 mg/100 g |
| β-carotene | 7.44 mg/100 g |
| total ascorbic acid | 2 mg/100 g |
| total tocopherol | 15.8 mg/100 g. |

EXAMPLE 3

Production for Producing Oily Liniment by Powdering in Oil:

6.0 kg of green tea leaves, which had been dried to give a moisture content of 5% or less, were powdered in a friction grinder to give an average grain diameter of about 15 µm. Then 15 kg (16.7 l) of coconut oil was added thereto and the resultant mixture was finely powdered in a wet-type ultra-fine friction grinder (Supermasscolloider MKZA8-10™ manufactured by Masuko Sangyo, Co., Ltd., Saitama; grinder size 150 mm) for about 11 minutes to thereby give a mixture of fine tea leaf powder of about 4 to 10 µm in grain diameter with coconut oil. During the powdering procedure, the coconut oil temperature was elevated from 16° C. to 43° C. After the completion of the powdering, the mixture was supplied into a continuous centrifuge (TOMO-E DECANTER PTM006™, manufactured by Tomoe Engineering Co., Ltd., Tokyo; 6000 rpm, 3200 G, treating temperature 80° C., liquid supply rate 50 l/h) so as to separate the supernatant from the solid matters. Thus, a slightly greenish oily solution (RUN-1) was obtained. Moreover, the separation procedure was performed by using the same apparatus (6000 rpm, 3200 G, treatment temperature 50° C., liquid supply rate 50 l/h) and thus another slightly greenish oily solution (RUN-2) was obtained. The obtained oily solutions are usable as a oily liniment base.

The oily solutions thus obtained were analyzed by high performance liquid chromatography. The results are as follows:

|  | RUN-1 | RUN-2 |
| --- | --- | --- |
| epicatechin | 28 mg/100 g | 34 mg/100 g |
| epigallocatechin | 110 mg/100 g | 140 mg/100 g |
| epicatechin gallate | 27 mg/100 g | 32 mg/100 g |
| epigallocatechin gallate | 120 mg/100 g | 140 mg/100 g |
| β-carotene | 7.40 mg/100 g | 7.33 mg/100 g |
| total ascorbic acid | 4 mg/100 g | 5 mg/100 g |
| total tocopherol | 15.6 mg/100 g | 15.6 mg/100 g. |

When the antibacterial effects of the obtained oily solutions were examined, it was observed that these oily solutions showed antibacterial effects against *Escherichia coli* O-157, methicillin-resistant *Staphylococcus aureus* (MRSA) and fungi.

INDUSTRIAL APPLICABILITY

The oily cosmetics according to the present invention show little so-called stickiness, which is often shown by oily cosmetics, but impart a dry feel in using. In addition, these oily cosmetics can contain the tea leaf components at a high concentration without resort to emulsifiers, etc. Therefore, they can be safely used even by consumers highly sensitive to chemicals without any fear of skin irritation. Because of containing the tea leaf components at a high concentration, moreover, these oily cosmetics have sufficient antibacterial and deodorizing effects. Thus, they can be used in protecting sick persons' skin and maintaining cleanness. They are also efficacious in treating bedsore. In case of hair care products, an antidandruff effect can be also achieved. Furthermore, these oily cosmetics are expected as exerting an effect of preventing atopic dermatitis.

The invention claimed is:

1. A process for producing an oily cosmetic containing tea leaf components, comprising mixing and stirring preliminarily ground tea leaves having an average grain diameter of approximately 15 µm in a dried state into an oily base, then further grinding said oily base mixture by means of a wet-type ultra fine friction grinder until grains of said tea leaves have a diameter of 1 to 10 µm to thereby encourage migration of said tea leaf components comprising catechins to the oily base, and subsequently eliminating powder residuals of said tea leaves.

2. The process for producing an oily cosmetic as claimed in claim 1, characterized in that said grinding treatment is carried out for 5 to 20 minutes by means of a wet-type ultra-fine friction grinder.

3. The process for producing an oily cosmetic as claimed in claim 1, characterized in that elimination of said powder residuals of said tea leaves is carried out by filtration or centrifugation.

4. The process for producing an oily cosmetic as claimed in claim 1, characterized in that said oily base is any one of a vegetable oil, a mineral oil or a mixture thereof.

5. The process for producing an oily cosmetic as claimed in claim 1, characterized in that said catechins are selected from the group consisting of epicatechin, epigallocatechin, epicatchin gallate and epigallocatechin gallate.

* * * * *